(12) United States Patent
Jabri

(10) Patent No.: US 8,306,268 B2
(45) Date of Patent: Nov. 6, 2012

(54) METHOD AND SYSTEM FOR IMAGE INTEGRITY DETERMINATION

(75) Inventor: Kadri Nizar Jabri, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1453 days.

(21) Appl. No.: 11/854,118

(22) Filed: Sep. 12, 2007

(65) Prior Publication Data

US 2009/0067667 A1 Mar. 12, 2009

(51) Int. Cl.
*G06K 9/00* (2006.01)
(52) U.S. Cl. ........................ 382/104; 382/131
(58) Field of Classification Search .................. 382/100, 382/128–132, 104
See application file for complete search history.

(56) References Cited

U.S. PATENT DOCUMENTS

| 5,809,161 | A  | * | 9/1998  | Auty et al. ................. 382/104 |
| 7,084,903 | B2 |   | 8/2006  | Narayanaswami et al. |
| 2003/0228042 | A1 | * | 12/2003 | Sinha ........................ 382/131 |

* cited by examiner

*Primary Examiner* — Hadi Akhavannik
(74) *Attorney, Agent, or Firm* — Fletcher Yoder, P.C.

(57) ABSTRACT

A method and system for determining integrity of images is disclosed herein. The method includes determining the integrity of a non-image data of an image file. The method of protecting images comprises: obtaining an image file having both image data and non-image data and generating at least one code based on the non-image data at the time of creation of the image file. The code is incorporated into the image data of the image file in a visually non-detectable format. In an example, a digital watermarking technique is used to incorporate the code into the image data.

14 Claims, 6 Drawing Sheets

METHOD AND SYSTEM FOR IMAGE INTEGRITY DETERMINATION

FIELD OF THE INVENTION

The present invention relates generally to image integrity. More particularly, this invention relates to, a system and method for determining integrity of non-image data pertaining to an image file.

BACKGROUND OF THE INVENTION

Generally images are generated and stored in the form of an image file having two components: the first component being an image data comprising pixel values that are capable of creating a visual image and the second component being a non-image data related to image parameters, image information properties, conditions, patient identification information, instrument manufacture information, technology information, etc. The non-image data can be stored in an image header or in an image trailer.

In the case of medical images as well, the images acquired include image data and non-image data. The medical images are generally stored in Digital Imaging and Communications in Medicine ("DICOM") format. The non-image data could be stored in a header; the header does not contain pixel information, but contains other information such as the exact technique factors used during the image acquisition. The integrity of this other information, as it relates to a particular image, can be important in evaluating imaging security or quality of care at a specific institution. For example, investigators reviewing the quality of care provided to a patient may use the image data along with the non-image data during the course of a malpractice lawsuit.

The images acquired using different imaging systems and stored in different formats could be manipulated easily. In fact the image data and non-image data could be manipulated in different ways after the image has been stored and/or during transfer of the image file electronically or physically. Such manipulation can adversely affect the integrity of the image data, and make it difficult or impossible to rely on its accuracy.

Today, image-watermarking techniques can be used on image data to hide confidential or authorship information for the image. However there are no mechanisms to protect or detect manipulation of the non-image data. Today, one can read an image file, edit a non-image data associated with the image, and then re-save the image file. However, there is currently no way to identify or prevent the manipulation of the non-image data, thereby putting the integrity of the data into question. There are many lawsuits (e.g., malpractice lawsuits) which involve issues concerning manipulation or authenticity of the images and various other properties of the images. Thus securing the header information, which carries the non-image data of an image file, is very essential.

Thus, there exists a need to provide a method and system to determine the integrity of the non-image data and/or image data in an image file.

SUMMARY OF THE INVENTION

The above-mentioned shortcomings, disadvantages and problems are addressed herein which will be understood by reading and understanding the following specification.

One embodiment of the present invention provides a method of determining integrity of images. The method comprises: obtaining an image file having both image data and non-image data; generating at least one code based on the non-image data at the time of creation of the image file; and incorporating the code into the image data such that the code is not visually detectable. The method of determining the integrity of the images may further include verifying the integrity of the non-image data whenever required.

In another embodiment, a method of verifying the integrity of an image is provided. The method comprises: reading a code from an image data, the code being created and incorporated in the image data at the time of creation of an image file, based on non-image data of the image file. The method also comprises: regenerating at least one code during the time of verification of the image file, based on the non-image data available in the image file. The method further comprises: comparing the code incorporated in the image data of the image file with the regenerated code.

In yet another embodiment of the invention a computer program product stored in a computer readable media for protecting integrity of an image is disclosed. The computer program product comprises: a routine for generating a code based on the non-image data in an image file, and a routine for incorporating the code into the image data in a visually non-detectable form. In an embodiment, a digital image watermarking technique is used to incorporate the code in the visually non-detectable manner.

Various other features, objects, and advantages of the invention will be made apparent to those skilled in the art from the accompanying drawings and detailed description thereof.

BRIEF DESCRIPTION OF THE DRAWINGS

A clear conception of the advantages and features constituting inventive arrangements, and of various construction and operational aspects of typical mechanisms provided by such arrangements, are readily apparent by referring to the following illustrative, exemplary, representative, and non-limiting figures, which form an integral part of this specification, in which like numerals generally designate the same elements in the several views, and in which.

DETAILED DESCRIPTION OF THE INVENTION

Figure 1:
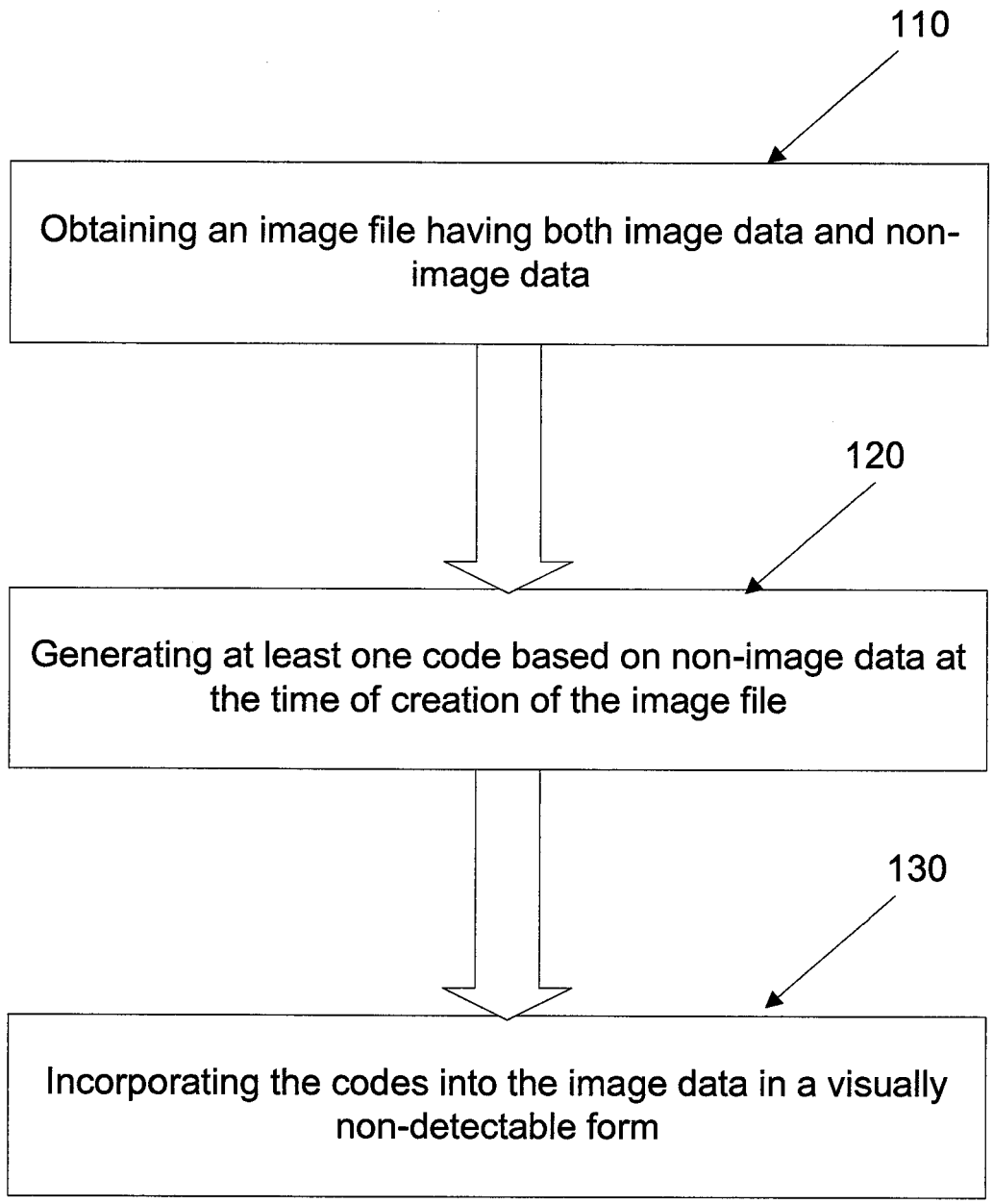
FIG. 1 is flowchart illustrating a method of determining integrity of images as described in an embodiment of the invention.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

In various embodiments, a method for protecting integrity of images is disclosed. The method includes determining integrity of non-image data in an image file. The method generates at least one unique code corresponding to the non-image data at the time of creation of the image file and incorporates or stamps the code on the image data. In an example the code is embedded in the image data using a watermarking technique. This technique will incorporate the code in the image data such that the code is not visually detectable when the image is displayed. The method comprises identifying the integrity of the images and/or verifying the same with earlier integrity information.

In another embodiment the invention provides a method of verifying the integrity of the image files. The image file includes non-image data and image data. At the time of creation of the image file, at least one code is generated corresponding to the non-image data and is incorporated in the image data. At the time of integrity verification, the code is regenerated based on the non-image data available in the image file and compared with the code incorporated in the image data of the image file.

In an embodiment, the invention provides a method to identify manipulation of the non-image data pertaining to an image file. The method includes stamping the image data of an image file in a visually non-identifiable manner with a code created at the time of creation of the image file, the code being created based on the non-image data of the image file. Also, this embodiment of the invention helps to detect the manipulation of the image data as well as the code incorporated in the image data.

In an embodiment the invention provides a method of protecting the integrity of medical images. The medical images are stored in DICOM format and include image data and non-image data. The image data includes pixel information and the non-image data includes image parameters, image information properties, conditions, patient identification information, instrument manufacture information, technology information, etc.

While the present technique is described herein with reference to medical images, it should be noted that the invention is not limited to this or any particular application or environment. Rather, the technique may be employed in a range of images wherein the image file includes image data as well as non-image data.

FIG. 1 is a flow chart illustrating a method of determining integrity of images as described in an embodiment of the invention. The method includes generating a code corresponding to the non-image data in an image file that needs to be protected or identified from manipulation, and incorporating the same in a visually non-detectable format in the image data of the image file. At step 110, an image file is obtained. The image file includes image data and non-image data. The images are acquired using an acquisition or imaging system, and can be stored in different formats. One of the formats includes DICOM image format, which is commonly used for medical images. The image data of the image file includes pixel information, which conveys the visual information of the image file. The non-image data may include image attributes, information about imaging techniques, imaging parameters, information about the imaged object/patient, etc. Determining the integrity of the non-image data in an image file is essential in various applications, as that will indicate the authenticity of the image files.

At step 120 at least one code is created based on the non-image data. The code is a unique code based on the non-image data and is created at the time of creation of the image file. At step 130, the code created at the time of creation of the image file is incorporated into the image data of the image file. The code can be incorporated in many ways to the image data. One way to incorporate the code is by embedding the code into the image data using watermarking techniques. The code is incorporated in the image data such that it is visually non-detectable when the image data is displayed. Thus the code incorporated in the image data will help to identify any manipulation of the non-image data. To verify the integrity of the image file, the code is regenerated using a similar technique by which the code is generated at the time of creation of the image file. The code incorporated in the image data is compared with the regenerated code and any discrepancy in the codes gives an indication of manipulation of the non-image data in the image file.

Figure 2:
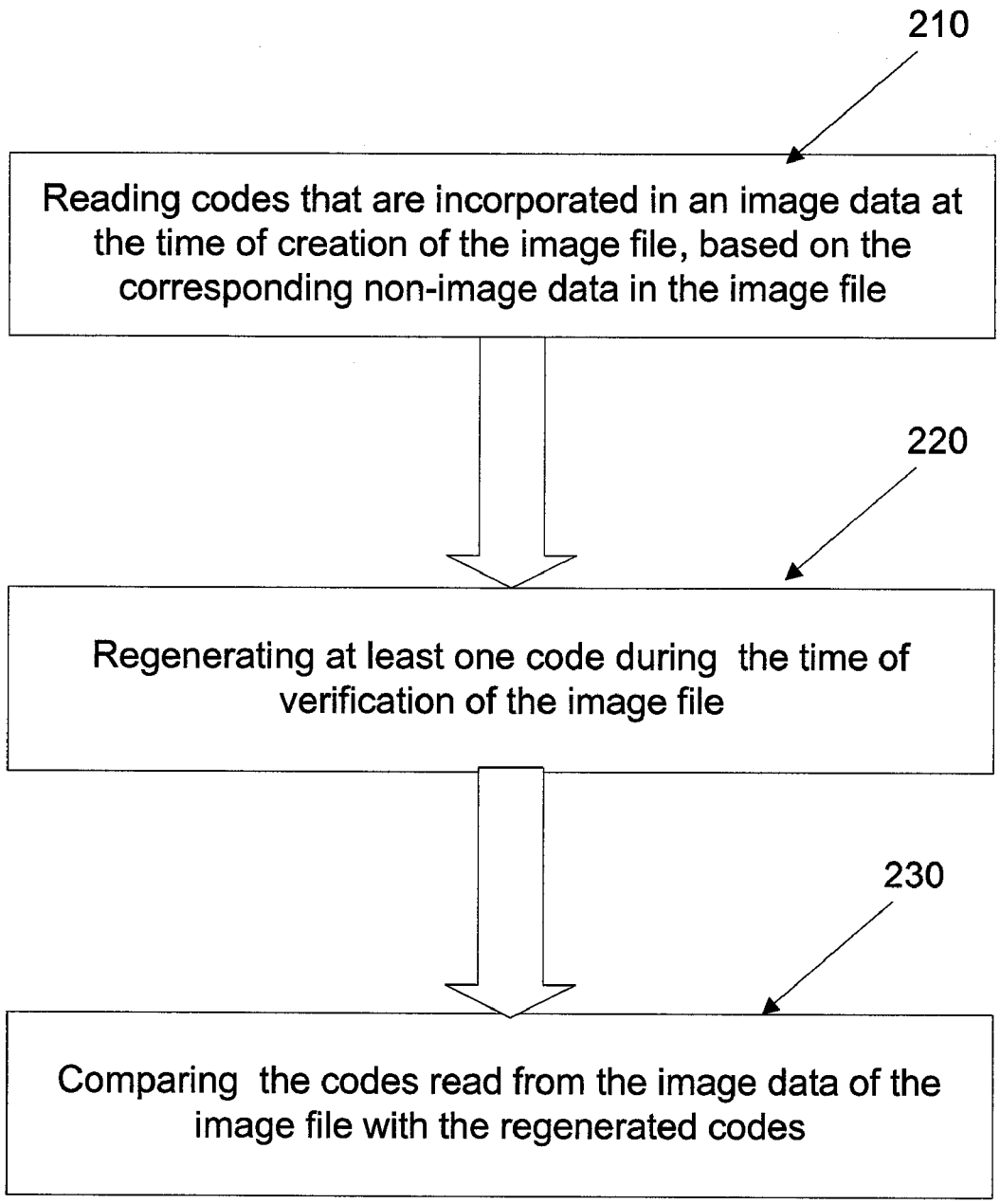
FIG. 2 is flowchart illustrating a method of verifying integrity of images as described in an embodiment of the invention.

FIG. 2 is flowchart illustrating a method of verifying integrity of images as described in an embodiment of the invention. The method illustrates verifying the integrity of non-image data in an image file. At step 210, at least one code incorporated in the image data of an image file is read. The code is created based on the non-image data, at the time of creation of the image file and is incorporated in the image data in a visually non-detectable format. In an example, a digital image watermarking technique may be used to incorporate the code into the image data.

At step 220, at least one code is regenerated based on the non-image data available in the image file at the time of verification of the image integrity. The code is regenerated using a similar technique that is used in the creating the code at the time of creation of the image file. At step 230, the code read from the image data of the image file and the regenerated code are compared. Any discrepancy in the codes will indicate the manipulation of the image file, which may include the manipulation of the non-image data and/or the image data. Upon identifying the discrepancy, an indication is generated. The discrepancy can be due to manipulation of the non-image data and/or the image data. Once the non-image data in the image file is manipulated the regenerated code will not match with the code incorporated in the image data. In another example, the image data may be manipulated and this may result in corruption of the code embedded in the image data. In this event as well, the comparison result will indicate a discrepancy and will generate an indication suggesting that the image file has been manipulated. Thus manipulation of the image file including manipulation of the image data and the non-image data can be identified by this method.

Figure 3:
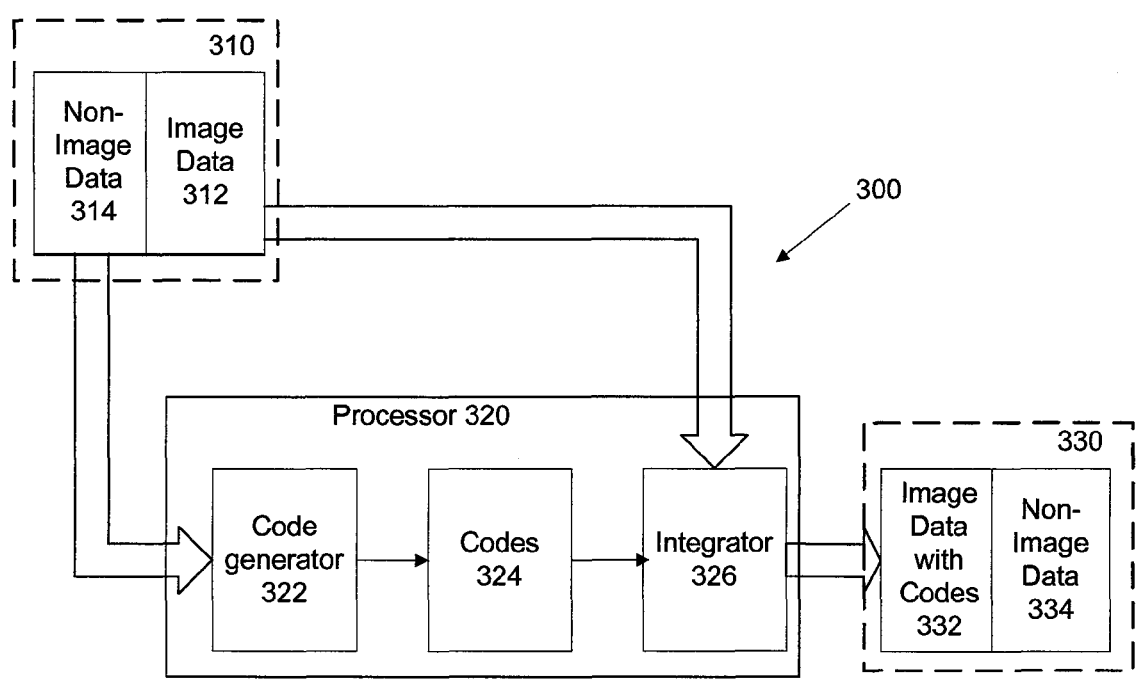
FIG. 3 is block diagram illustrating an image integrity determination system as described in an embodiment of the invention.

FIG. 3 is block diagram illustrating an image integrity securing system 300 as described in an embodiment of the invention. An image file 310 is generated or acquired from an imaging system or any other image storage device. The image file 310 includes an image data 312 and non-image data 314. The image data 312 includes pixel information that conveys the visual information of the image file. The non-image data 314 may include information about different imaging parameters, imaging techniques, image attributes, etc. In other words, the non-image data 314 may have all other information about the image file 310 other than the pixel information. The system 300 is provided with a processor 320, which will process the image file 310 for determining the integrity of the image file 310. The processor 320 is provided with a code generator 322 and an integrator 326. The code generator 322 generates a code 324 at the time of creation of an image file 310 based on the non-image data 314. The code 324 is a unique code that identifies the non-image data 314 of the image file 310. The integrator 326 is coupled with the code generator 322. The integrator 326 receives the image file 310 and the codes 324 from the code generator 322 and the codes 324 are incorporated in the image data 312 of the image file 310. Thus the processor 320 generates a stamped image 330 with an image data 332 embedded with the code 324 that gives information about the non-image data 312 and a non-image data 334. The codes 324 are incorporated in the image data 312 in a visually non-detectable format and will help in determining the integrity of the image file 310, especially the non-image data 314 in the image file 312.

Figure 4:
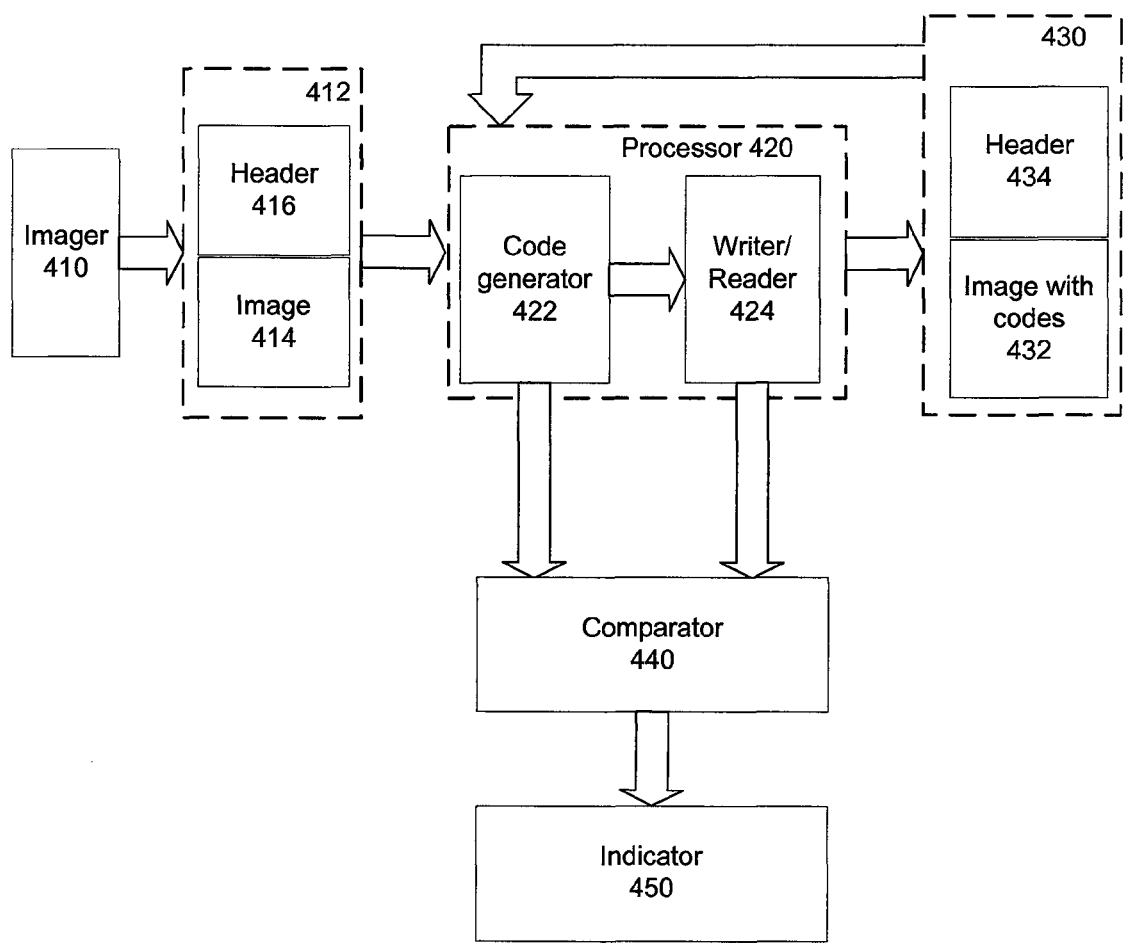
FIG. 4 is a medical imaging system implemented with an image integrity determination technique described in an embodiment of the invention.

FIG. 4 is a medical imaging system implemented with an image integrity determination technique described in an embodiment of the invention. The medical images are acquired by a medical imaging system, which essentially includes an imager 410. The medical imaging system can be an X-ray system, Computer Tomography (CT) Imaging System, Magnetic Resonance Imaging System, Ultrasound Imaging System etc, but need not be limited to these. Generally medical images are stored as DICOM images 412. The DICOM images 412 comprise image data and non-image data. The image data, referred to as image 414 hereinafter in this embodiment, includes pixel information of the image file 412, and the non-image data, hereinafter in this embodiment referred to as header information 416, includes information about imaging parameters, patient information, image attributes, imaging techniques, patient identification, etc.

The DICOM image file 412 including the image 414 and the header information 416 is fed to a processor 420. The processor 420 is configured to include a code-generator 422 and a reader/writer 424. The code generator 420 generates a unique code based on the non-image data or the header information 416 available in the header of the DICOM image file 412. The code is generated at the time of creation of the image file 412. At the time of creation of the image file 412, the reader/writer 424 acts as a writer and will incorporate the code generated by the code generator 422 into the image 414 of the image file 412. One example of the code is a Cyclic Redundancy Check ("CRC") code, but it need not be limited to this. The code is incorporated into the image 414 such that it is visually non-detectable. Different techniques could be used to achieve this, and one example is digital image watermarking techniques. Once the code is incorporated in a visually non-detectable format, a stamped DICOM image 430 is generated and manipulation of the header information in the stamped image 430 can be identified. The stamped image 430 includes an image with codes 432 and header information 434. At the time of verification of integrity of the header information 434, the corresponding stamped image 430 is fed to the processor 420. The code incorporated in the stamped image 430 is read from the image 432. The reader/writer 424 will act as a reader and will read the image 432 and extract the code incorporated in the image 432. At the time of verification of the header information 416, the code generator 422 provided with the stamped image 430 may regenerate at least one code based on the available header information 434. The codes read from the image 432 and the code regenerated based on the available header information 434 are fed to a comparator 440. The comparator 440 compares the codes and in case of any discrepancy an indicator 450 output from the comparator 440 generates an indication of the discrepancy. The discrepancy may indicate that either the header information of the stamped image is manipulated or the code incorporated in the image of the stamped image is manipulated. Thus by identifying the manipulation of the image file, the authenticity and integrity of the image file is verified.

Figure 5:
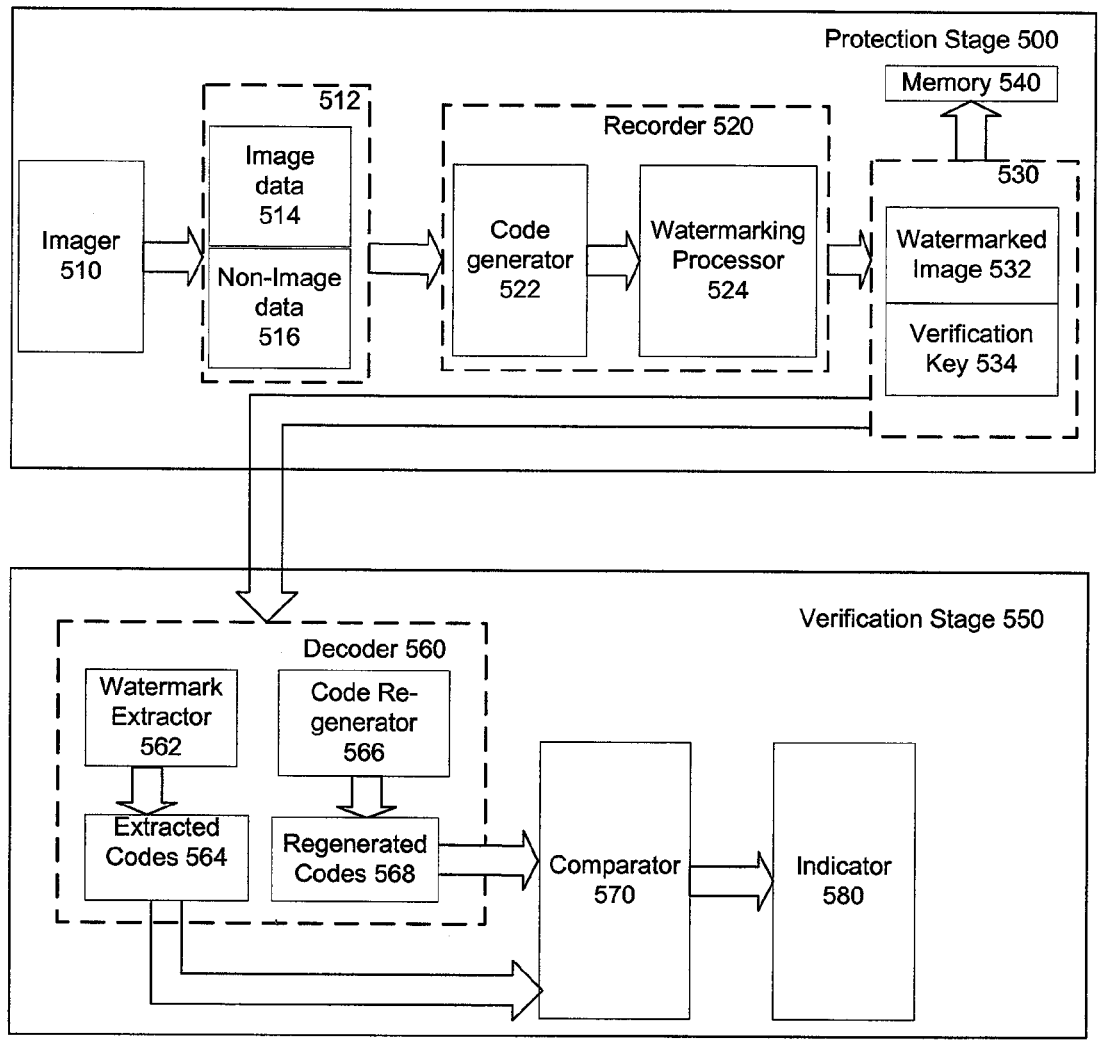
FIG. 5 is an image protection system as described in an embodiment of the invention.

FIG. 5 is an image protection system as described in an embodiment of the invention. The image protection system comprises a protection stage 500 and a verification stage 550. The protection stage 500 applies one or more image stamping techniques to the image and the verification stage 550 verifies the integrity of the stamped images. The protection stage 500 includes image creation or acquisition and stamping the images for identifying any manipulation of the images. An imager 510 is configured to provide or acquire image files 512. The imager 510 could be any imaging system including a medical imaging system or different cameras. The image files 512 include image data 514 and non-image data 516. The image data 514 include pixel information and the non-image data 516 include various other information such as image attributes, imaging parameters and imaging techniques. In case of camera, the non-image data may include camera parameters such as location, orientation, shutter speed, f-stop, etc. In case of medical imaging applications, the non-image data may include patient identification information, confidential information about the patient etc. The non-image data 516 includes any information other than the pixel information of the image file 512. The image data 514 and non-image data 516 of the image file 512 can be subject to various unwanted or unauthorized manipulations. The non-image data 516 may reveal important information about the image file 512 and manipulation of the same may destroy the integrity of the image file 512.

To identify manipulation of the image file 512, especially the manipulation of the non-image data 516, an embodiment of the invention involves generating a code corresponding to the non-image data 516 and incorporating the code in the image data 514. This is done at the time of creation of the image file and is achieved through a recorder 520. The image file 512 acquired or generated is fed to the recorder 520. The recorder 520 includes code generator 522 and a watermarking processor 524. The code generator 522 generates a unique code based on the non-image data 516. The code generator 522 provides the code to the watermarking processor 524 and the watermarking processor 524 incorporates the code to the image data 514 of the image file 512. The watermarking processor 524 incorporates the code to the image data 514 using a digital image watermarking technique, such that it is visually non-detectable. Thus the watermarking processor 524 generates a stamped image 530, which includes a watermarked image 532 and a verification key 534. The watermarked image 532 includes image data with a code embedded in the image data and the non-image data. The watermarking processor 524 at the time of applying watermarking techniques generates the verification key 534. The verification key 534 helps to read or extract the code incorporated in the watermarked image 532 at a later stage. The stamped image 530 may be stored in a memory 540. The stamped image 530 may also be sent to different destinations using different techniques.

The verification of the stamped images 530 is done at the verification stage 550. The verification stage 550 may be located any where such as it could be with a receiver that receives the stamped image 530 or with a memory, which is stored with the stamped images 530. The verification stage 550 includes a decoder 560 for extracting the code from the watermarked image 532. The decoder 560 comprises a watermark extractor 562 and a code re-generator 566. Using a verification key 534, the watermark extractor 562 extracts the code embedded in a visually non-detectable manner in the image data 532. The extracted code 564 represents the non-image data 516 that was present in the image file 512 at the time of creation of the image file. The code re-generator 566 regenerates at least one code based on the available non-image data with the watermarked image 532. The regenerated code 568 represents the non-image data available with the stamped image 530. The extracted code 564 from the image data of the stamped image 530 and the regenerated code 568, regenerated from the non-image data of the stamped image 530 are fed to a comparator 570. The comparator 570 compares the codes 564 and 568 and, if there is a discrepancy, an indication is generated by an indicator 580. The indicator 580 is output from the comparator 570 and gives an indication about the integrity of the image file based on comparison results.

Figure 6:
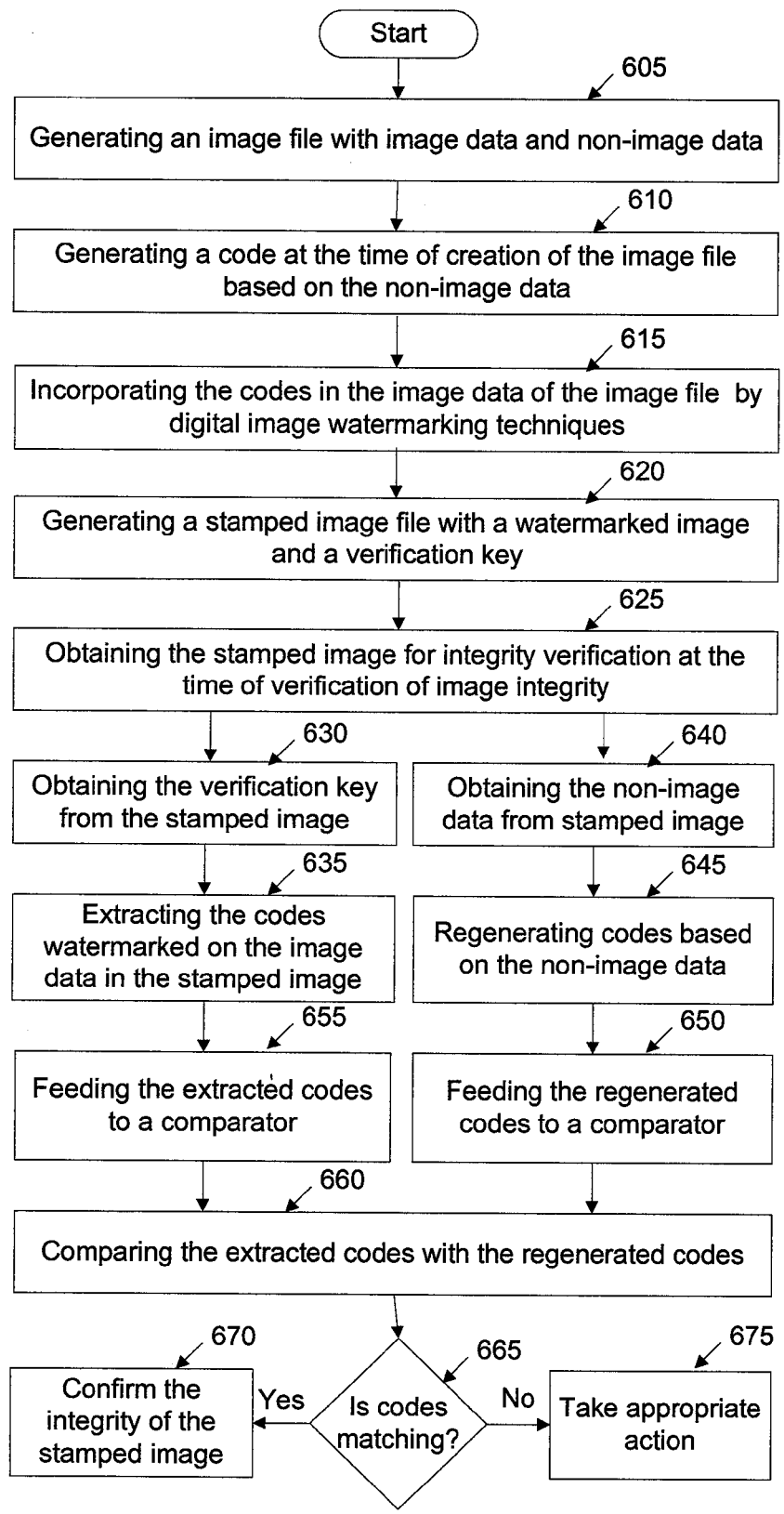
FIG. 6 is a flowchart illustrating the image protection method as described in an embodiment of the invention.

FIG. 6 is a flowchart illustrating the image protection method as described in an embodiment of the invention. The image protection method includes stamping the image with a code and checking the code for verifying the integrity of the image. At step 605, an image file is generated. The image file includes image data and non-image data. The image data includes pixel information and the non-image data includes other information about the image file. At step 610, at least one code is generated based on the non-image data in the image file. The code is generated at the time of creation of the image file. The code will represent the non-image data in the image file at the time of creation of the image file and any corruption of the non-image data and/or image data will give an indication about the integrity of the image file, especially the non-image data of the image file. At step 615, the code is incorporated into the image data using a digital image watermarking technique. The code is incorporated such that it is not visually detectable to a human being. At step 620, a stamped image is created. The stamped image includes a watermarked image having an image data with a code corresponding to the non-image data embedded on it and non-image data. The stamped image also includes a verification key, which will help to identify and read the codes watermarked on the image data.

At step 625, the stamped image is fetched from a source, at the time of verification of the image file. At step 630, the verification key is obtained from the stamped image. At step 635, with the help of the verification key, the code watermarked in the image data of the stamped image is extracted. At step 640, from the stamped image, non-image data is obtained. At step 645, at least one code is regenerated from the non-image data obtained from the stamped image. At steps 650 and 655, the regenerated code and the extracted code are fed to a comparator. At step 660, the comparator compares the extracted code with the regenerated code. A check 665 is made to check whether the codes are matching. If the codes match, the integrity of the image is confirmed, and the method gives an indication that the image file, more specifically the non-image data is not manipulated, as indicated by step 670. If the codes mismatch, the method gives an indication that the non-image data in the image file is manipulated and appropriate action needs to be taken, as indicted by step 675. The steps 605 to 620 are performed at the time of protection or stamping of the image integrity and steps 625 to 675 are performed at the time of verification of the image integrity.

In an embodiment of the invention a computer program product stored in a computer readable media for protecting integrity of an image is disclosed. The computer program product comprises: routine for generating a code based on the non-image data in an image file and a routine for incorporating the codes into the image data in visually non-detectable form. The routine for generating the code comprises: generating a unique code corresponding to the non-image data at the time of creation of the image file and the routine for incorporating the codes includes digital image watermarking techniques. The computer program product may further comprise a routine for verifying the integrity of the image file. The routine for verifying may include a routine for regenerating the codes based on the non-image data available in the image file, at the time of verification of the image file integrity and routine for reading the incorporated codes in the image data and comparing the read codes with the regenerated codes.

Some of the advantages of the invention include increased protection of the image. The method will help to identify the manipulation of the image data and based-on that appropriate actions can be taken to prevent or correct the manipulation.

Thus various embodiments of the invention describe image protection method and system. The method and system determines the manipulation of the non-image data and/or image data in an image file. This will help in identifying the integrity and authenticity of the images.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

I claim:

1. A method of determining integrity of images, comprising:
   obtaining a Digital Imaging and Communications in Medicine ("DICOM") image file having both image data and non-image data;
   generating at least one code based on the non-image data in the DICOM image file;
   incorporating the code into the image data such that the code is not visually detectable; and
   verifying the integrity of the image by regenerating the at least one code based on the non-image data available in the DICOM image file and comparing the code incorporated in the image data with the regenerated code.

2. A method as in claim 1, wherein the step of obtaining the DICOM image file comprises: acquiring an image and incorporating the image data in a DICOM image file.

3. A method as in claim 1, wherein the image data includes pixel information providing a visual image, and the non-image data includes image attributes and parameters.

4. A method as in claim 1, wherein the step of incorporating the code comprises: stamping the code into the image data using digital image watermarking, the stamped code being visually non-detectable.

5. A method as in claim 1, wherein the step of verifying further comprises: identifying manipulation of the image data and the non-image data in the DICOM image file.

6. A method of verifying the integrity of an image comprising:
   reading a code from an image data, the code being created and incorporated in the image data at the time of creation of a DICOM image file, based on non-image data of the DICOM image file;
   regenerating at least one code during the time of verification of the DICOM image file, based on the non-image data available in the DICOM image file; and
   comparing the code incorporated in the image data of the DICOM image file with the regenerated code.

7. A method as in claim 6, wherein the code read from the image data is incorporated in the image data using a digital image watermarking technique, in a visually non-detectable format.

8. A method as in claim 6, further comprising: generating an indication upon detection of manipulation of the image data or the non-image data.

9. A method as in claim 8, further comprising: generating the indication based on changes in the image data, including manipulation of the code incorporated in the image data and manipulation of pixel information conveyed in the image data.

10. A method as in claim 8, further comprising: generating the indication upon identifying manipulation of the non-image data available in the DICOM image file at the time of verification of the DICOM image file.

11. A computer program product stored on a non-transitory computer readable medium comprising:
- a routine for generating a code based on the non-image data in a DICOM image file;
- a routine for incorporating the code into the image data in a visually non-detectable form;
- a routine for regenerating the code based on the non-image data in the DICOM image file, at the time of verification of the DICOM image file integrity; and
- a routine for reading the incorporated code in the image data and comparing the read code with the regenerated code.

12. A computer program product as in claim 11, wherein the routine for generating the code comprises: generating a unique code corresponding to the non-image data at the time of creation of the DICOM image file.

13. A computer program product as in claim 11, wherein the routine for incorporating the code includes a digital image watermarking technique.

14. A computer program product as in claim 11, further comprising: a routine for verifying the integrity of the DICOM image file.

* * * * *